US012502449B2

(12) United States Patent
Tsai et al.

(10) Patent No.: US 12,502,449 B2
(45) Date of Patent: Dec. 23, 2025

(54) DISINFECTION APPARATUS

(71) Applicant: ADATA TECHNOLOGY CO., LTD., New Taipei (TW)

(72) Inventors: Yu-Syuan Tsai, New Taipei (TW); Kuo-Ting Chung, Taoyuan (TW); Chien-Ta Tseng, Kaohsiung (TW); Chia-Hsiang Hsiao, New Taipei (TW)

(73) Assignee: ADATA TECHNOLOGY CO., LTD., New Taipei (TW)

( * ) Notice: Subject to any disclaimer, the term of this patent is extended or adjusted under 35 U.S.C. 154(b) by 485 days.

(21) Appl. No.: 18/075,421

(22) Filed: Dec. 6, 2022

(65) Prior Publication Data

US 2023/0181784 A1 Jun. 15, 2023

Related U.S. Application Data

(60) Provisional application No. 63/289,639, filed on Dec. 15, 2021.

(30) Foreign Application Priority Data

Nov. 30, 2022 (TW) ................................ 111145857

(51) Int. Cl.
*A61L 2/26* (2006.01)

(52) U.S. Cl.
CPC ............. *A61L 2/26* (2013.01); *A61L 2202/20* (2013.01)

(58) Field of Classification Search
CPC ............................... A61L 2/26; A61L 2202/20
See application file for complete search history.

(56) References Cited

U.S. PATENT DOCUMENTS

2016/0221195 A1 8/2016 Ashworth
2021/0361794 A1* 11/2021 Yencho .................... A61L 2/26

FOREIGN PATENT DOCUMENTS

| | | | |
|---|---|---|---|
| CN | 1575742 | A | 2/2005 |
| CN | 204864170 | U | 12/2015 |
| CN | 109432466 | A | 3/2019 |
| CN | 109568623 | A | 4/2019 |
| CN | 111317836 | A | 6/2020 |
| CN | 111376268 | A | 7/2020 |
| CN | 113788088 | A | 12/2021 |
| KR | 20110102606 | A | 9/2011 |
| KR | 20170123910 | A | 11/2017 |
| TW | M604205 | U | 11/2020 |
| WO | 2007065033 | A2 | 6/2007 |

* cited by examiner

*Primary Examiner* — Sean E Conley

(57) ABSTRACT

A disinfection apparatus is adapted to disinfect a floor and includes a body and a disinfection assembly. The body is adapted to move along a default path via a moving device. The moving device is positioned at a bottom of the body and includes at least two floor contact parts. The floor contact parts are adapted to contact with the floor and form floor contact points on the floor, and the floor contact points form a track with actuation of the floor contact parts. The disinfection assembly is installed at the bottom of the body and is adapted to at least disinfect the track. Therefore, the disinfection apparatus is prevented from polluting an environment during disinfection.

6 Claims, 5 Drawing Sheets

DISINFECTION APPARATUS

FIELD OF THE INVENTION

The present invention relates to a disinfection apparatus, and more particularly to a disinfection apparatus which can move by itself and disinfect a surrounding environment during the movement.

BACKGROUND OF THE INVENTION

To maintain the cleanness of public places and prevent the spread of diseases, especially in hospitals where there are many patients, the environment must be cleaned and disinfected frequently. To reduce the workload of personnel, it is an appropriate choice to introduce a robot that may move by itself and disinfect the environment through a disinfection apparatus installed. In this way, easy-to-clean regions (such as floors) are handed over to the robot for cleaning, and the personnel only need to focus on difficult-to-clean parts (such as chairs) for disinfection, such that the burden of personnel can be greatly reduced.

However, unlike human soles which can be easily lifted up for disinfection or directly replaced shoes, a moving device such as wheels of the robot is more difficult to disinfect or replace due to positions, which makes it possible for germs to spread in the environment with movement of the robot.

SUMMARY OF THE INVENTION

The present invention provides a disinfection apparatus which can be prevented from becoming a way of disease spreading.

To achieve the above advantages, an embodiment of the present invention provides a disinfection apparatus adapted to disinfect a floor and including a body and a disinfection assembly. The body is adapted to move along a default path via a moving device. The moving device is positioned at a bottom of the body and includes at least two floor contact parts. The floor contact parts are adapted to contact with the floor and form at least two floor contact points on the floor. The two floor contact points form a track with actuation of the floor contact parts. The disinfection assembly is installed at the bottom of the body and is adapted to disinfect the track of the floor contact parts or the floor contact points.

In an embodiment of the present invention, an accommodating space is formed in the bottom and is adapted to accommodate the moving device. The accommodating space includes a bottom surface and an inner side wall surface surrounding the bottom surface. The disinfection assembly includes a first disinfection unit and a second disinfection unit. The first disinfection unit is installed on the inner side wall surface and faces an inner side of the accommodating space. The first disinfection unit is adapted to act on a disinfected region in the accommodating space. The second disinfection unit is installed on the bottom surface and is adapted to face the floor to act on the track.

In an embodiment of the present invention, the at least two floor contact points are separated by a spacing in a direction perpendicular to the default path. The body has a front side wall surface positioned in front of the moving device and a back side wall surface positioned behind the moving device along the default path. The disinfection assembly includes a first disinfection unit and a second disinfection unit. The first disinfection unit is installed at a bottom of the front side wall surface and is adapted to generate a first disinfection zone on the floor. The first disinfection zone is positioned in front of the body along the default path. A width of the first disinfection zone is greater than or equal to the spacing. The second disinfection unit is installed at a bottom of the back side wall surface and is adapted to generate a second disinfection zone on the floor. The second disinfection zone is positioned behind the body along the default path. A width of the second disinfection zone is greater than or equal to the spacing such that the track is covered during movement of the disinfection apparatus.

In an embodiment of the present invention, the first disinfection zone and the second disinfection zone respectively project a first projection and a second projection on the floor. The body projects a body projection on the floor. The first projection and the second projection are adjacent to the body projection.

In an embodiment of the present invention, the disinfection apparatus further includes a protective device installed on the front side wall surface. An edge of the protective device is positioned in front of the first disinfection unit in a direction parallel to the default path.

In an embodiment of the present invention, the disinfection assembly further includes a third disinfection unit and a fourth disinfection unit. The third disinfection unit is close to a top end of the front side wall surface and is positioned above the first disinfection unit. The fourth disinfection unit is close to the back side wall surface and is positioned above the second disinfection unit.

In an embodiment of the present invention, the disinfection assembly further includes a fifth disinfection unit. The body further includes a middle side wall surface positioned between the front side wall surface and the back side wall surface. The fifth disinfection unit is installed on the middle side wall surface to disinfect a part beyond the default path.

According to the above description, the disinfection apparatus in the present invention can prevent viruses or bacteria from spreading through the moving device of the disinfection apparatus, because the disinfection assembly for at least disinfecting the track passed by the floor contact parts of the disinfection apparatus or even the floor contact parts is provided at the bottom of the disinfection apparatus.

DETAILED DESCRIPTION OF PREFERRED EMBODIMENTS

Hereinafter, the terms used in the description of the embodiments according to the present invention, such as the description of orientational or positional relationships indicated by "up", "down", and the like, are described according to the orientational or positional relationships shown in the figures used. The above terms are only intended to conveniently describe rather than to limit the present invention, that is to say, they do not indicate or imply that the elements mentioned must have specific orientations or be constructed in specific orientations. In addition, the terms "first", "second", and the like mentioned in this specification or the scope of the patent application are only used to name the elements or distinguish different embodiments or scopes, rather than to limit the upper or lower limit of the number of elements.

Figure 1:
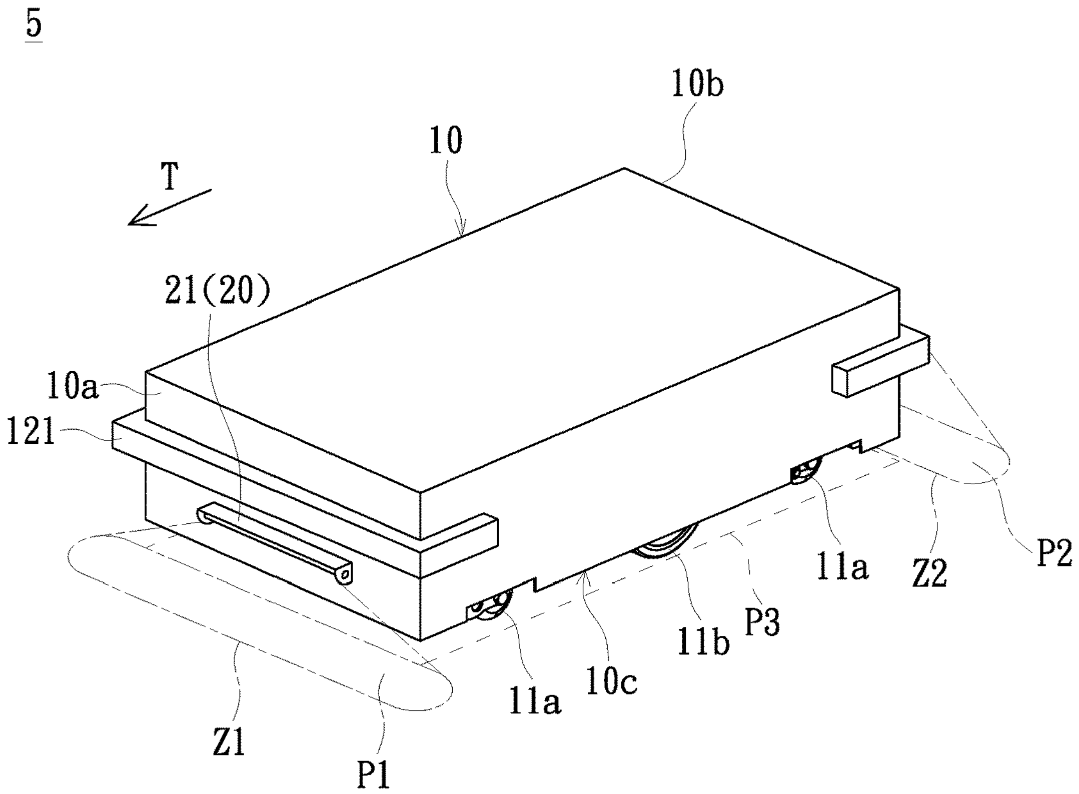
FIG. 1 is a schematic three-dimensional view of a front surface of a disinfection apparatus according to an embodiment of the present invention.
Figure 2:
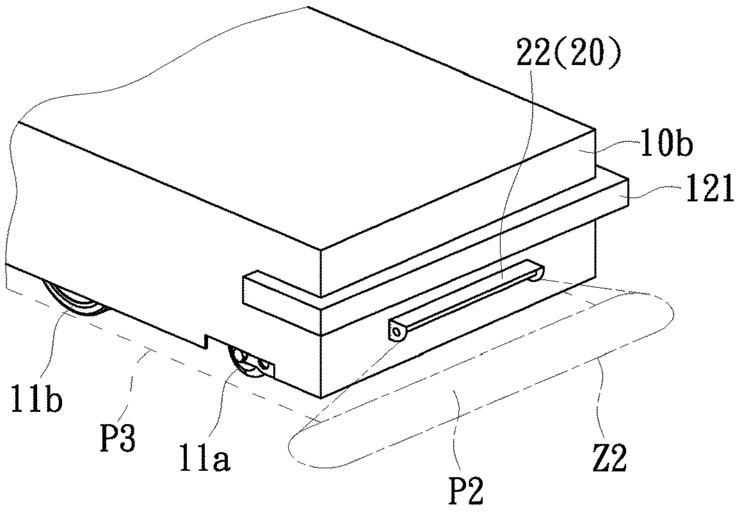
FIG. 2 is a schematic three-dimensional view of a back surface of the disinfection apparatus according to the embodiment shown in FIG. 1.
Figure 3:
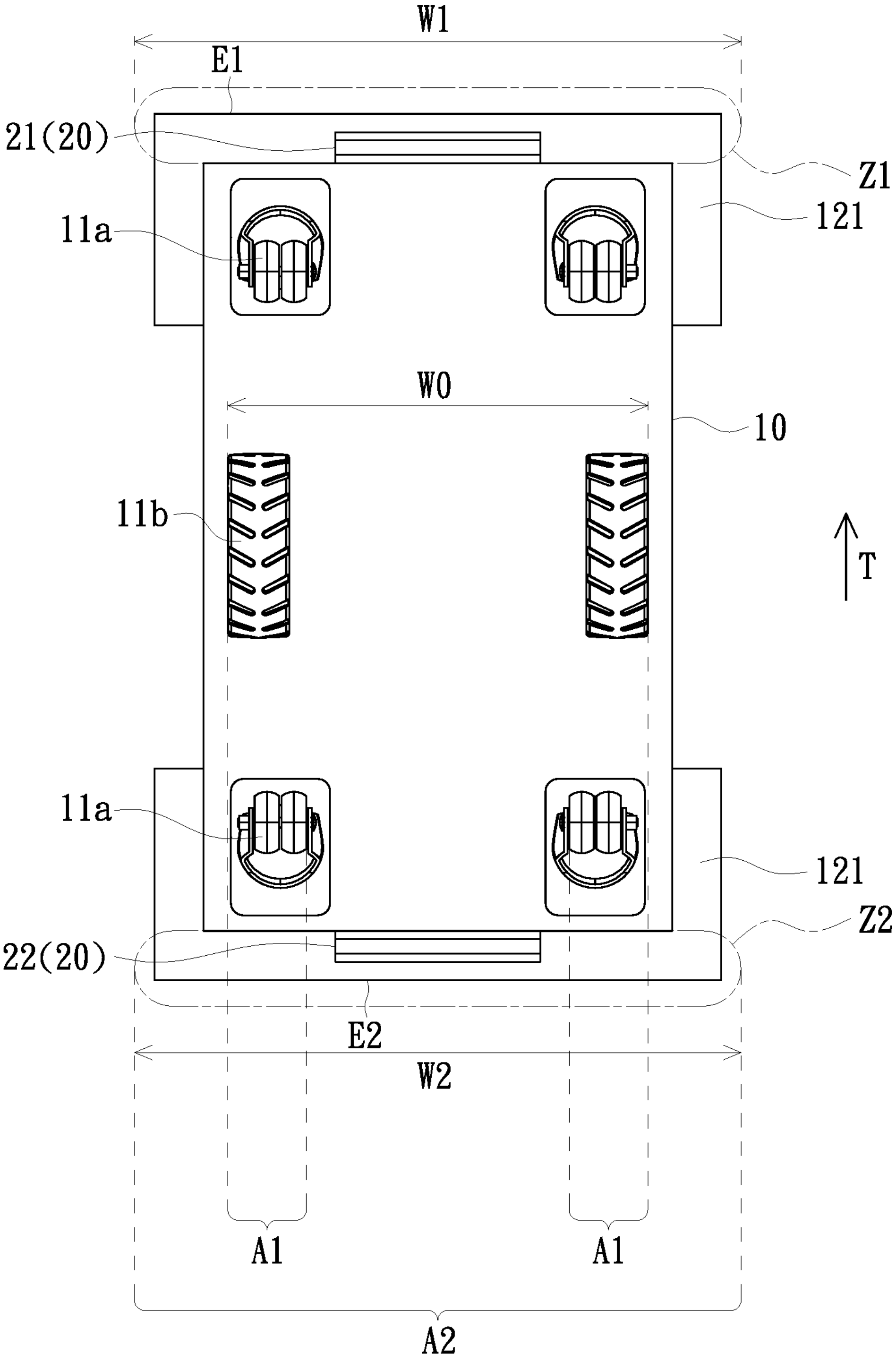
FIG. 3 is a schematic bottom view of movement of the disinfection apparatus according to the embodiment shown in FIG. 1.

FIG. 1 is a schematic three-dimensional view of a front surface of a disinfection apparatus according to an embodiment of the present invention, FIG. 2 is a schematic three-dimensional view of a back surface of the disinfection apparatus according to the embodiment shown in FIG. 1, and FIG. 3 is a schematic bottom view of movement of the disinfection apparatus according to the embodiment shown in FIG. 1. Referring to FIG. 1 to FIG. 3, a disinfection apparatus 5 in this embodiment is adapted to disinfect a floor. The disinfection apparatus 5 includes a body 10 and a disinfection assembly 20. The body 10 is adapted to move along a default path T via a moving device. The moving device is positioned at a bottom of the body 10 and includes at least two floor contact parts. The floor contact parts are, for example, four floor contact rollers 11*a* and two driving rollers 11*b* of the moving device in FIG. 1. The driving rollers 11*b* are adapted to drive the disinfection apparatus 5 to move according to the default path T, and the floor contact rollers 11*a* are adapted to provide support for maintaining the moving device to stably contact with the floor. The floor contact parts (the floor contact rollers 11*a* and the driving rollers 11*b*) are adapted to contact with the floor and form at least two floor contact points (positions of contact between the floor and the floor contact rollers 11*a* and between the floor and the driving rollers 11*b*) on the floor, and the floor contact points will form a track (seeing a region A1 in FIG. 3) with actuation of the floor contact parts. The disinfection assembly 20 is installed at the bottom of the body 10 and is adapted to disinfect the track of the floor contact parts (the floor contact rollers 11*a* and the driving rollers 11*b*) or the floor contact points.

In this embodiment, the disinfection assembly 20 includes a first disinfection unit 21 and a second disinfection unit 22. The two floor contact points are separated by a spacing W0 in a direction perpendicular to the default path T. The body 10 has a front side wall surface 10*a* positioned in front of the moving device and a back side wall surface 10*b* positioned behind the moving device along the default path T. The first disinfection unit 21 is installed on the front side wall surface 10*a* and is adapted to generate a first disinfection zone Z1 on the floor. The first disinfection zone Z1 is positioned in front of the body 10 along the default path T, and a width W1 of the first disinfection zone Z1 is, for example, greater than the spacing W0 between the two floor contact points (e.g., the two floor contact rollers 11*a* or the two driving rollers 11*b*), as shown in FIG. 3. The second disinfection unit 22 is installed on the back side wall surface 10*b* and is adapted to generate a second disinfection zone Z2 on the floor during operation. The second disinfection zone Z2 is positioned behind the body 10 along the default path T. As shown in FIG. 3, a width W2 of the second disinfection zone Z2 is, for example, greater than the spacing W0 between the two floor contact points (e.g., the two floor contact rollers 11*a* or the two driving rollers 11*b*).

In this configuration as shown in FIG. 1 and FIG. 3, the first disinfection zone Z1 and the second disinfection zone Z2 will move forward with the movement of the body 10 when the body 10 moves, the rollers 11*a* and 11*b* of the moving device will pass through a region passed by the first disinfection zone Z1, and the region A1 (i.e. the track) passed by the rollers 11*a* and 11*b* of the moving device will be covered by a region A2 passed by the second disinfection zone Z2. That is to say, a region to be contacted by the moving device can be disinfected via the first disinfection zone Z1, and the region A1 (the track of the floor contact points) passed by the floor contact rollers 11*a* and the driving rollers 11*b* of the moving device can be disinfected via the second disinfection zone Z2, so as to prevent germs from spreading because of the disinfection apparatus 5. In addition, it is ensured that the two floor contact points still can be disinfected in other embodiments of the present invention in which the width W0 of the two floor contact points in the direction perpendicular to the default path T may be equal to the width of the first disinfection zone Z1 and the width of the second disinfection zone Z2.

In this embodiment as shown in FIG. 1, the moving device is, for example, positioned on a bottom surface 10*c* of the body 10. In the plurality of rollers included in the moving device, the driving rollers 11*b* are, for example, driven by a drive device (not shown in figure) positioned inside the body 10 to drive the body 10 to move. The default path T may be, for example, a path preset by a user of the disinfection apparatus 5, or may be, for example, a path planned by the disinfection apparatus 5 according to a map and a path planning program stored in an internal memory device (not shown in figure).

The first disinfection unit 21 and the second disinfection unit 22 are, for example, ultraviolet disinfection apparatuses for disinfection via short-wave ultraviolet (UVC) or disinfection spray mechanisms for sterilization via a disinfectant. During installation, the first disinfection unit 21 protrudes from the front side wall surface 10*a*, such as a position close to the bottom of the body 10, and the second disinfection unit 22 protrudes from the back side wall surface 10*b*, such as a position close to the bottom of the body 10. As shown in FIG. 1 and FIG. 2, the first disinfection unit 21 and the second disinfection unit 22 are shown in embodiments of UVC lamp tubes. Through this configuration, when the first disinfection unit 21 is actuated, a part of light generated by the first disinfection unit 21 will irradiate the floor to form the first disinfection zone Z1 and also will irradiate the front side wall surface 10*a* to disinfect the body 10. Similarly, when the second disinfection unit 22 is actuated, a part of light generated by the second disinfection unit 22 will irradiate the floor to form the second disinfection zone Z2 and also will irradiate the back side wall surface 10*b* to disinfect the body 10.

In other words, through this configuration shown in FIG. 1 and FIG. 2, the first disinfection zone Z1 and the second disinfection zone Z2 project a first projection P1 and a second projection P2 on the floor, respectively. According to a positional relationship among the first projection P1, the second projection P2, and a body projection P3 projected by the body 10 on the floor, the first projection P1 and the second projection P2 are adjacent to the body projection P3, which can eliminate disinfection dead angles between the first disinfection zone Z1 and the body 10 and between the second disinfection zone Z2 and the body 10. In addition, through this configuration, the front side wall surface 10*a* and the back side wall surface 10*b* may prevent the disinfection apparatus from directly irradiating the moving device positioned on the bottom surface 10*c* of the body 10. In some embodiments where rubber is, for example, used as the floor contact rollers 11*a* or the driving rollers 11*b* of the moving device, the degradation of a material of the floor contact rollers 11*a* or the driving rollers 11*b* may be avoided.

In this embodiment as shown in FIG. 1, the body 10 further includes a protective device 121 installed on the front side wall surface 10*a*. The protective device 12 is, for example, a protective strip arranged on the front side wall surface 10*a*, and at least one edge E1 of the protective device 121 is positioned in front of the first disinfection unit 21 in a direction parallel to the default path T. In this way, when an object collides with the disinfection apparatus 5 from the front of the disinfection apparatus 5, it will first collide with the protective device 121 to avoid damage to the first disinfection unit 21 installed on the front side wall surface 10*a*.

In addition, in this embodiment as shown in FIG. 2, the body 10 also includes a protective device 121 installed on the back side wall surface 10*b*. The protective device 121 is, for example, a protective strip arranged on the back side wall surface 10*b*, and at least one edge E2 of the protective device 121 is positioned behind the second disinfection unit 22 in the direction parallel to the default path T. In this way, when an object collides with the disinfection apparatus 5 from the back of the disinfection apparatus 5, it will first collide with the protective device 121 to avoid damage to the second disinfection unit 22 installed on the back side wall surface 10*b*.

In conclusion, because the first/second disinfection unit (21 or 22) capable of generating the first/second disinfection zone (Z1 or Z2) towards the front/back of the disinfection apparatus 5 is arranged in front of/behind the disinfection apparatus 5, and the width W1 or W2 of the first/second disinfection zone (Z1 or Z2) in the direction perpendicular to the default path T is greater than or equal to the spacing W0 between the two floor contact points of the moving device in contact with the floor in the direction perpendicular to the default path T, the disinfection apparatus 5 according to the embodiment of the present invention, in addition to disinfecting the environment in the front while moving, can ensure that the rollers of the moving device in contact with the floor are also disinfected by the second disinfection zone Z2 to prevent viruses or bacteria from spreading through the moving device of the disinfection apparatus 5.

Figure 4:
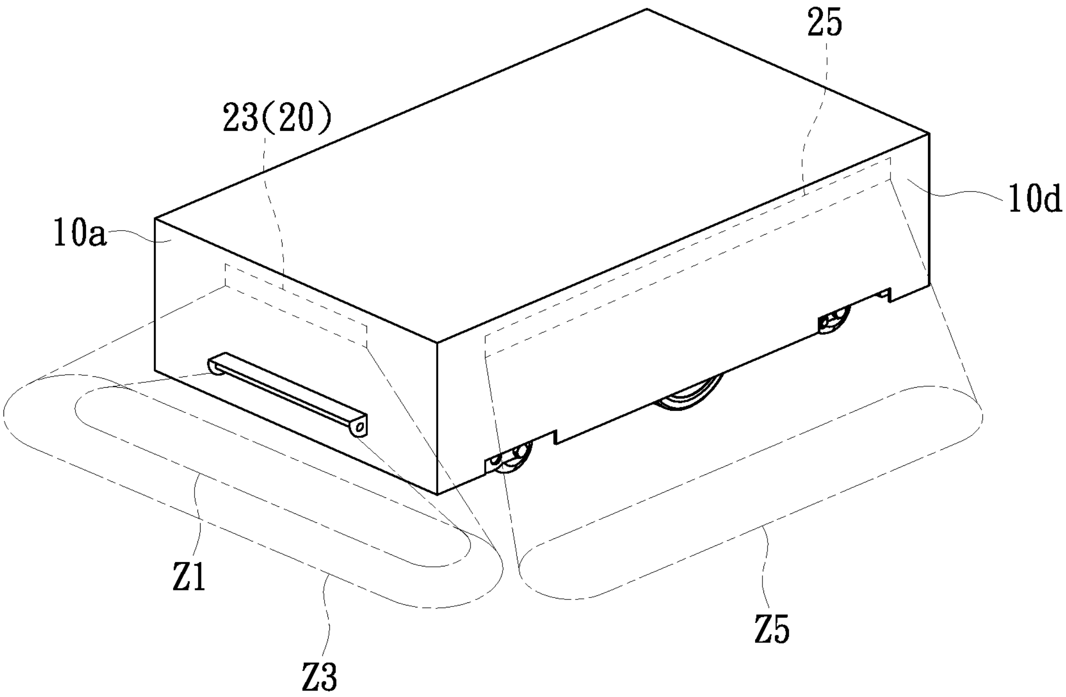
FIG. 4 is a schematic three-dimensional view of a front surface of a disinfection apparatus according to another embodiment of the present invention.
Figure 5:
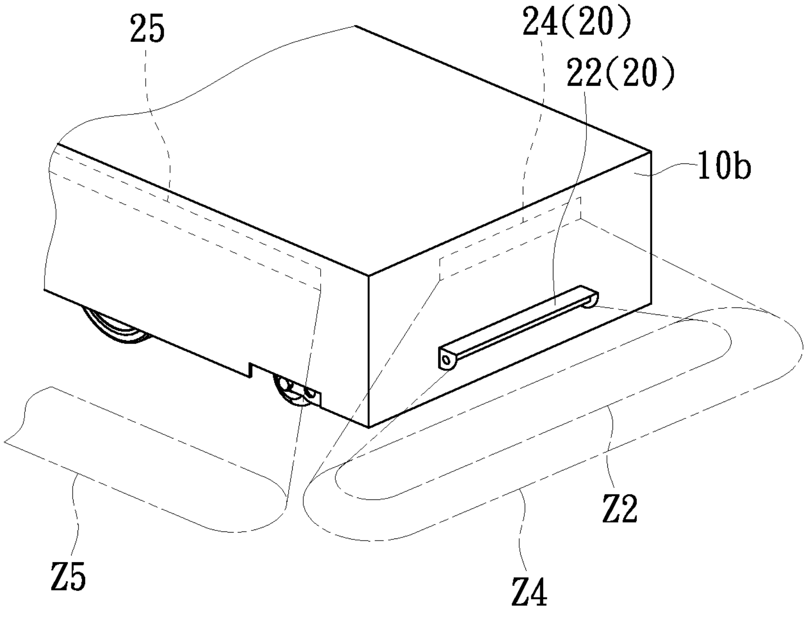
FIG. 5 is a schematic three-dimensional view of a back surface of the disinfection apparatus according to the embodiment shown in FIG. 4.

FIG. 4 is a schematic three-dimensional view of a front surface of a disinfection apparatus according to another embodiment of the present invention, and FIG. 5 is a schematic three-dimensional view of a back surface of the disinfection apparatus according to the embodiment shown in FIG. 4. Because the details of the body 10, the first disinfection unit 21 and the second disinfection unit 22 are similar to those in the above-mentioned embodiments, no redundant detail is to be given herein. The following only describes the differences between the embodiment shown in FIG. 4 and the embodiment shown in FIG. 1. In this embodiment as shown FIG. 4 and FIG. 5, the disinfection apparatus 5 further includes a third disinfection unit 23, a fourth disinfection unit 24, and a fifth disinfection unit 25.

In this embodiment as shown in FIG. 4 and FIG. 5, the third disinfection unit 23 is arranged on the front side wall surface 10*a* and is positioned above the first disinfection unit 21, for example, at a position close to a top of the front side wall surface 10*a*. The fourth disinfection unit 24 is arranged on the back side wall surface 10*b* and is positioned above the second disinfection unit 22, for example, at a position close to a top of the back side wall surface 10*b*. The fifth disinfection unit 25 is arranged on a middle side wall surface 10*d* positioned between the front side wall surface 10*a* and the back side wall surface 10*b* of the body 10, for example, at a position close to a top end of the middle side wall surface 10*d*.

Through this configuration, the third disinfection unit 23, the fourth disinfection unit 24 and the fifth disinfection unit 25 generate the third disinfection zone Z3, the fourth disinfection zone Z4 and the fifth disinfection zone Z5 on the floor when started, respectively. The third disinfection unit 23 increases an area of the disinfection zone positioned in front of the body 10, the fourth disinfection unit 24 increases an area of the disinfection zone positioned behind the body 10, and the fifth disinfection unit 25 increases a disinfection area of the floor positioned on a side surface of the body 10. In addition, because of the position, the disinfection apparatus 5 can disinfect a surface of the body 10 by starting the third disinfection unit 23, the fourth disinfection unit 24, and the fifth disinfection unit 25 close to a top of the body 10.

Figure 6A:
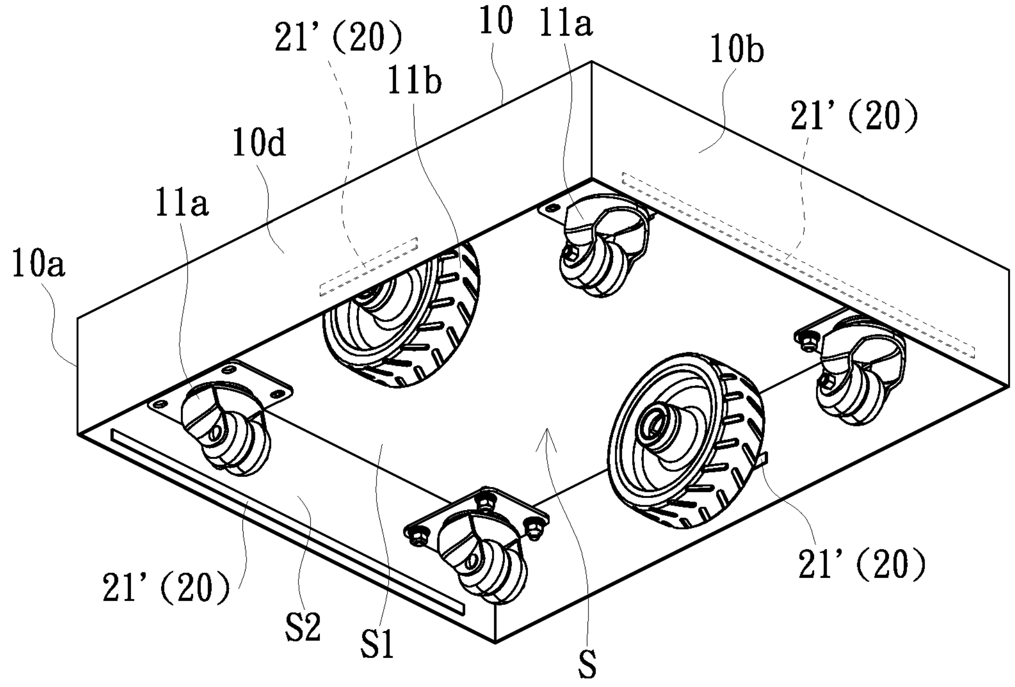
FIG. 6A is a schematic three-dimensional view of a bottom surface of a disinfection apparatus according to another embodiment of the present invention.
Figure 6B:
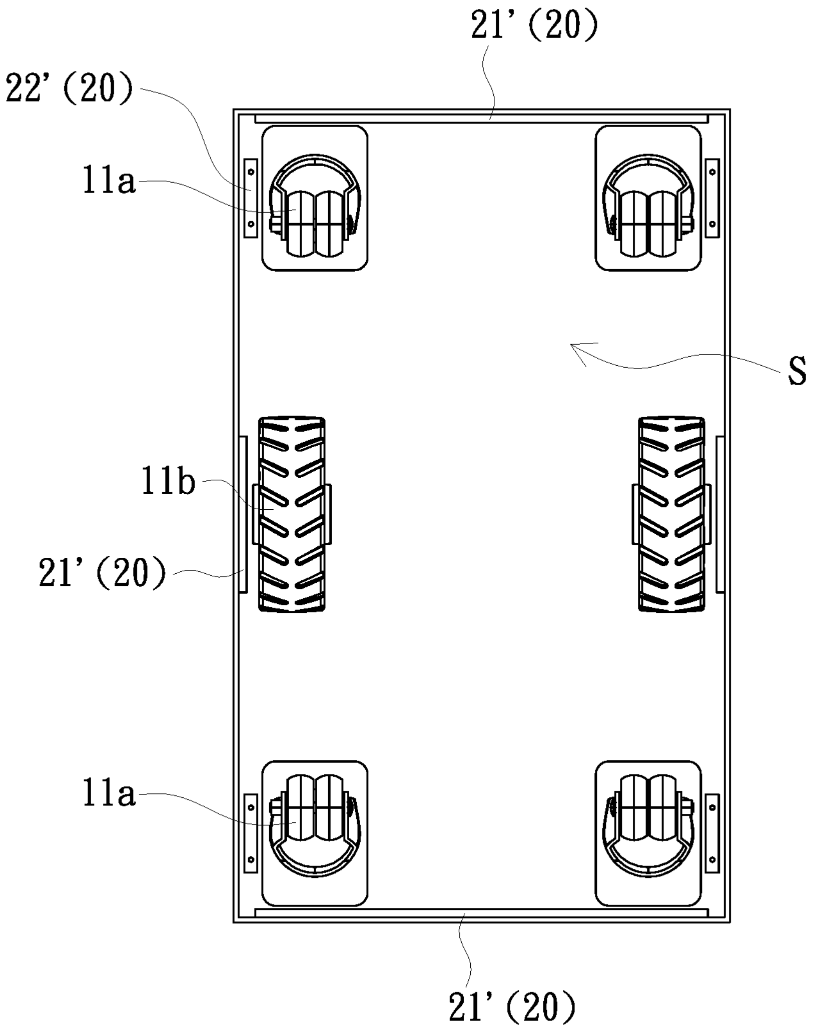
FIG. 6B is a schematic bottom view of FIG. 6A.

FIG. 6A is a schematic three-dimensional view of a bottom surface of a disinfection apparatus according to another embodiment of the present invention, and FIG. 6B is a schematic bottom view of FIG. 6A. In this embodiment, because the content of the moving device may refer to the above-mentioned embodiments, no redundant detail is to be given herein. An accommodating space S is formed in the bottom of the body 10. The accommodating space S is adapted to accommodate the moving device. The accommodating space S includes a bottom surface S1 and an inner side wall surface S2 surrounding the bottom surface S1. The disinfection assembly 20 includes a first disinfection unit 21' and a second disinfection unit 22'. The first disinfection unit 21' is installed on the inner side wall surface S2 and faces an inner side of the accommodating space S. The first disinfection unit 21' is adapted to act on a region (which may be referred to as a disinfected region) in the accommodating space S. The second disinfection unit 22' is installed on the bottom surface S1 and is adapted to face the floor to act on the track.

In this embodiment as shown in FIG. 6A and FIG. 6B, the first disinfection unit 21' includes, for example, four disinfection lamp strips, but the type is not limited. Herein, two of the four disinfection lamp strips are arranged on the inner side wall surface S2 close to an inner side of the middle side wall surface 10*d* and are adjacent to the driving rollers 11*b*, and the other two disinfection lamp strips are respectively arranged on the inner side wall surface S2 close to the front side wall surface 10*a* and the inner side wall surface S2 close to the back side wall surface 10*b*, and irradiate the accommodating space S and the moving device (the driving rollers 11*b* and the floor contact rollers 11*a*). The disinfection lamp strips are, for example, light-emitting diode (LED) lamp strips capable of releasing the UVC. When the first disinfection unit 21' is started, it irradiates the two driving rollers 11*b*, the four floor contact rollers 11*a*, and the accommodating space S, such that the accommodating space S inside the body 10 becomes the disinfected region disinfected by the first disinfection unit 21'. The second disinfection unit 22' includes, for example, four disinfection lamp strips arranged on the bottom surface S1 and facing the floor, but the type is not limited. The disinfection lamp strips are respectively adjacent to the respective floor contact rollers 11*a*. The disinfection lamp strips are, for example, the LED lamp strips capable of releasing the UVC. When the second disinfection unit 22' is started, in addition to irradiating the floor to disinfect the floor contact rollers 11*a* and the track of the floor contact points of the floor, the second disinfection unit 22' also disinfects the driving rollers 11*b* and the floor contact points of the floor during the movement of the disinfection apparatus 5, because the driving rollers 11*b* are positioned between the two floor contact rollers 11*a* along the default path T.

According to the above description, it is know that because the disinfection assembly for at least disinfecting the track passed by the floor contact parts of the disinfection apparatus or even the floor contact parts is provided at the bottom of the disinfection apparatus, the disinfection apparatus in an embodiment of the present invention can prevent the viruses or bacteria from spreading through the moving device of the disinfection apparatus.

What is claimed is:

1. A disinfection apparatus adapted to disinfect a floor, the disinfection apparatus comprising:

a body, adapted to move along a default path via a moving device, wherein the moving device is positioned at a bottom of the body and comprises at least two floor contact parts, the at least two floor contact parts are adapted to contact with the floor and form at least two floor contact points on the floor, and the at least two floor contact points form a track with actuation of the at least two floor contact parts; and a disinfection assembly, installed at the bottom of the body and adapted to at least disinfect the track;

wherein an accommodating space is formed in the bottom and is adapted to accommodate the moving device, the accommodating space comprises a bottom surface and an inner side wall surface surrounding the bottom surface, the disinfection assembly comprises a first disinfection unit and a second disinfection unit, the first disinfection unit is installed on the inner side wall surface and faces an inner side of the accommodating space, the first disinfection unit is adapted to act on a disinfected region in the accommodating space, and the second disinfection unit is installed on the bottom surface and is adapted to face the floor to act on the track.

2. A disinfection apparatus adapted to disinfect a floor, the disinfection apparatus comprising:

a body, adapted to move along a default path via a moving device, wherein the moving device is positioned at a bottom of the body and comprises at least two floor contact parts, the at least two floor contact parts are adapted to contact with the floor and form at least two floor contact points on the floor, and the at least two floor contact points form a track with actuation of the at least two floor contact parts; and a disinfection assembly, installed at the bottom of the body and adapted to at least disinfect the track;

wherein the at least two floor contact points are separated by a spacing in a direction perpendicular to the default path, the body has a front side wall surface positioned in front of the moving device and a back side wall surface positioned behind the moving device along the default path, the disinfection assembly comprises a first disinfection unit and a second disinfection unit, the first disinfection unit is installed at a bottom of the front side wall surface and is adapted to generate a first disinfection zone on the floor, the first disinfection zone is positioned in front of the body along the default path, a width of the first disinfection zone is greater than or equal to the spacing, the second disinfection unit is installed at a bottom of the back side wall surface and is adapted to generate a second disinfection zone on the floor, the second disinfection zone is positioned behind the body along the default path, and a width of the second disinfection zone is greater than or equal to the spacing such that the track is covered during movement of the disinfection apparatus.

3. The disinfection apparatus according to claim 2, wherein the first disinfection zone and the second disinfection zone respectively project a first projection and a second projection on the floor, the body projects a body projection on the floor, and the first projection and the second projection are adjacent to the body projection.

4. The disinfection apparatus according to claim 3, further comprising a protective device, installed on the front side wall surface, wherein at least one edge of the protective device is positioned in front of the first disinfection unit in a direction parallel to the default path.

5. The disinfection apparatus according to claim 2, wherein the disinfection assembly further comprises a third disinfection unit and a fourth disinfection unit, the third disinfection unit is close to a top end of the front side wall surface and is positioned above the first disinfection unit, and the fourth disinfection unit is close to the back side wall surface and is positioned above the second disinfection unit.

6. The disinfection apparatus according to claim 2, wherein the disinfection assembly further comprises a fifth disinfection unit, the body further comprises a middle side wall surface positioned between the front side wall surface and the back side wall surface, and the fifth disinfection unit is installed on the middle side wall surface to disinfect a part beyond the default path.

* * * * *